United States Patent [19]

Cassidy

[11] Patent Number: 4,912,989
[45] Date of Patent: Apr. 3, 1990

[54] SHOCK ABSORBING IMMERSION PROBE

[75] Inventor: John E. Cassidy, Churchville, Pa.

[73] Assignee: Electro-Nite International, Antwerp, Belgium

[21] Appl. No.: 263,568

[22] Filed: Oct. 27, 1988

[51] Int. Cl.⁴ ............................................. G01K 1/12
[52] U.S. Cl. .............................. 73/866.5; 73/DIG. 9; 374/140
[58] Field of Search ......... 73/DIG. 9, 864.53–864.59, 73/866.5; 374/26, 139, 140; 136/234; 226/99, 100

[56] References Cited

U.S. PATENT DOCUMENTS

| | | | |
|---|---|---|---|
| 3,463,005 | 8/1969 | Hance | 73/DIG. 9 |
| 4,003,814 | 1/1977 | Tarassoff et al. | 324/450 |
| 4,048,857 | 9/1977 | Bardenheuer et al. | 73/864.56 |
| 4,067,242 | 1/1978 | Judge | 73/DIG. 9 |
| 4,193,857 | 3/1980 | Bannister et al. | 264/63 |
| 4,528,849 | 7/1985 | Paschkis | 73/866.5 |
| 4,582,872 | 4/1986 | Hudgin et al. | 524/441 |
| 4,732,477 | 3/1988 | Kumbrant | 73/DIG. 9 |
| 4,778,281 | 10/1988 | Falk | 73/DIG. 9 |

FOREIGN PATENT DOCUMENTS 1008231  10/1965  United Kingdom ................ 374/139

Primary Examiner—Robert R. Raevis
Attorney, Agent, or Firm—Panitch, Schwarze, Jacobs & Nadel

[57] ABSTRACT

A shock absorbing immersion probe comprises a probe body having a first end portion for immersion into a molten metal bath, a second end portion coupleable to support means and means for detecting characteristics of a molten metal, where shock absorbing means are positioned proximate the first end of the probe body for absorbing impact loads imposed upon the first end portion of the probe. A polymer foam shock absorber for immersion probes is also disclosed, as well as methods for making the same.

13 Claims, 2 Drawing Sheets

SHOCK ABSORBING IMMERSION PROBE

BACKGROUND OF THE INVENTION

1. Field of the Invention

The present invention relates to immersion probes for analyzing molten metals and, more particularly, to shock absorbing immersion probes.

2. Description of the Prior Art

Immersion probes are currently used in the metal-making art for analyzing or detecting various characteristics of metal. Characteristics, such as temperature, viscosity, the temperature of solidification of the molten metal (liquidous arrest temperature), and carbon, oxygen and other component content, to name a few, are preferably ascertained in situ while the metal is in its molten state. Because of the high temperatures at which molten metals are maintained, analyses in the molten metal environment necessitate devices that can withstand such high temperatures without affecting their functionality during the immersion period.

Examples of probes for detecting characteristics of molten metals include those probes disclosed in U.S. Pat. Nos. 3,643,509, 3,656,338 and 4,557,152, for example. Generally, immersible probes comprise an elongate body defining a chamber in which certain detecting means may be housed, such as thermocouples and sampling chambers and other molten metal detecting devices. To protect the detecting means from the intense heat of the molten metal environment, the body typically comprises a fire-proof material, such as quartz, ceramic, heat-resistant cement, silica, carbon, graphite, sintered aluminum oxide, zirconium oxide, or magnesium oxide, or agglutinated sand. These materials, and their method of fabrication, are generally costly and, consequently, an immersion probe made therefrom is relatively expensive.

While these materials exhibit excellent heat-resistant properties, they are brittle and relatively fragile and may be cracked or otherwise damaged when subjected to mechanical shock forces or impact loads, such as when they are dropped or struck against a hard object.

In the course of normal use, an immersion probe is typically coupled to means for lowering and raising the immersion probe into and out of a molten metal bath. Generally, such raising and lowering means also comprises means for electrically coupling the detecting means in the immersion probe to remotely located processing or recording means, where characteristics of the molten metal bath may be examined by metal processing operators.

The immersion probe or lance is generally coupled to or plugged into a reciprocally receiving coupling device, such as a sub-lance or lance holder. These and other reciprocally receiving coupling devices are well known in the art and are widely used for quick coupling and uncoupling of such immersion probes. Once such probes are received within such coupling devices and prior to immersion into the molten metal, an operator generally performs a test to confirm that the probe has been properly electrically coupled and that the detecting means are properly functioning.

Occasionally, the immersion probe is not properly coupled because of bent or damaged couplings or contacts, incomplete electrical contact, or mechanical or other malfunctions. When the operator performs a pre-immersion test, the probe is indicated as being defective, even though the problem may be due only to improper engagement of electrical contacts. Because timing is often critical in metals-processing, it is normal for the metal processing operator to immediately reject the immersion probe and to couple another probe to avoid delay.

A rejected immersion probe is typically dropped into a retrieval area via a rejection chute, which directs the rejected immersion probe to an area where the probe comes to rest. It is common for the immersion probe to be damaged during its travel through the rejection chute because of the impact loads imposed on the probe body while moving, especially where (as is common) the probe stops abruptly at the lower end of the chute. The brittle body of the probe and particularly the fragile detecting means within the probe (generally positioned at the lower end of the probe) are often broken as a result of such impact, thereby precluding any further use for the probe.

A metal processing operator, while attempting to successfully couple an immersion probe, often rejects (and thereby destroys) several immersion probes until successful coupling is achieved. Because of this procedure, a large quantity of fully operable probes may be needlessly destroyed, resulting in unnecessarily increased costs.

The present invention overcomes many of the disadvantages inherent in the above-described immersion probes by providing shock absorbing means for absorbing impact loads imposed upon the immersion probe. The shock absorbing means of the present invention can be easily and relatively inexpensively attached to or molded onto the immersion probe. In addition, the shock absorbing means of the present invention does not substantially interfere with the detecting or analyzing means in the immersion probe. Moreover, use of the present invention results in considerable monetary savings by eliminating or lessening the damage to immersion probes caused by impact loads imposed upon the probe body, thereby permitting re-use of operable probes, which have been rejected due to minor coupling problems.

SUMMARY OF THE INVENTION

Briefly stated, the present invention comprises an immersion probe including a probe body having a first end portion for immersion into a molten metal bath and a second end portion, which is coupleable to support means, and means for detecting characteristics of a molten metal. The improvement of the present invention comprises shock absorbing means proximate the first end portion of the probe body for absorbing impact loads imposed upon the first end portion of the probe. In one embodiment, the shock absorbing means comprises a polymer foam shock absorber, which is positioned proximate the first end portion of the probe body. The polymer foam shock absorber is formed by molding and curing a polymer foam in engagement with and longitudinally extending from the first end portion.

BRIEF DESCRIPTION OF THE DRAWINGS

The foregoing summary of the invention, as well as the following detailed description of preferred embodiments, will be better understood when read in conjunction with the appended drawings. For the purpose of illustrating the invention, there is shown in the drawings embodiments which are presently preferred, it being understood, however, that the invention is not limited to the specific methods and instrumentalities disclosed. In the drawings.

DESCRIPTION OF THE PREFERRED EMBODIMENTS

Figure 1:
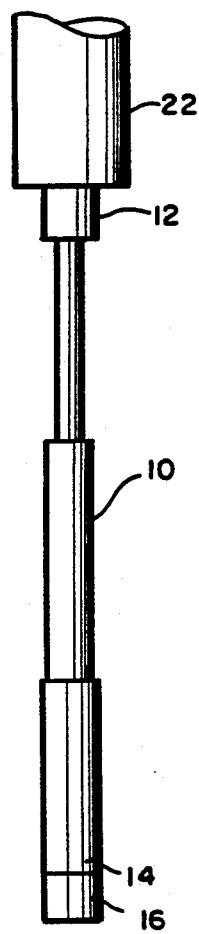
FIG. 1 is a side elevational view of an immersion probe which is coupled to support means and to which has been applied shock absorbing means in accordance with the present invention.

Referring to the drawings, wherein like numerals indicate like elements throughout, there is shown in FIG. 1 a side elevational view of an immersion probe comprising a elongated, generally cylindrical probe body 10 having a first end portion 14 (typically the bottom end when immersed in a molten metal) for immersion into a molten metal bath (not shown) and a second end portion 12 coupleable to support means 22. As used herein, the term "molten metal bath" will be understood to mean the molten metal bath environment, including the molten metal and slag that accumulates on or around the molten metal.

The immersion probe body 10 illustrated in FIG. 1 is typical of multi-lance type immersion probes generally known in the art. However, it should be clearly understood that the immersion probe body 10 to which shock absorbing means may be attached in accordance with the present invention may include other configurations and designs for immersion probes for use in detecting desired characteristics of molten metal.

The support means 22, which may comprise a pipe or cable, may be used to raise and lower the probe body 10 into and out of a molten metal bath. One example of such support means 22 is the sub-lance or sensor lance designed by the Nippon Steel Corp.

The probe body 10 may comprise fire-proof and/or melt-resistant materials, such as quartz, ceramics and other refractory materials known in the art for manufacturing immersion probe bodies intended for use in molten metal baths. The first end portion 14 of the immersion probe body 10 may comprise similar, but not necessarily the same materials as those comprising the remainder of the probe body 10. In addition, the probe body may comprise a paper tube or sleeve to protect or partially isolate the probe from the molten metal bath and from the heated gases that exist around and above the molten metal bath. One skilled in the art may readily determine the composition of the probe body 10 based on the particular intended use for the probe.

The immersion probe body 10 may have positioned therein means 15 for detecting characteristics of a molten metal. Such detection means or devices 15 are typically, although not necessarily, positioned proximate the first end portion 14 and may include, but are not limited to, thermocouple devices, such as the CD thermocouple, means for measuring certain element content and means for determining solidification temperature. The type and number of detection means 15 positioned within the probe body 10 may be readily determined by one skilled in the art based on the molten metal characteristic desired to be determined using the immersion probe.

According to the present invention, shock absorbing means 16 is positioned proximate the first end portion 14 of the probe body 10 for absorbing impact loads imposed upon the first end portion 14 of the immersion probe. It is preferred that the shock absorbing means 16 does not substantially interfere with the detecting means 15 in the immersion probe body 10. For example, in the embodiment of the present invention shown in FIGS. 1 and 2b, the shock absorbing means 16 dissolves upon insertion of the immersion probe into the molten metal bath or when exposed to the high temperatures in and around the molten metal bath. However, the shock absorbing means 16 need not dissolve upon insertion into a molten metal bath where the presence of the shock absorbing means 16 does not substantially interfere with the proper functioning of the detecting means 15 in a molten metal bath environment. For example, the shock absorbing means 16 may comprise a spring member, such as the coiled spring 24 illustrated in FIG. 5, or a retractable shock absorber strut (not shown) comprising a fire-proof material that neither dissolves upon immersion into a molten metal bath nor substantially interferes with the functioning of the detecting means 15 of the immersion probe.

It is presently preferred that the shock absorbing means 16 is formed of a material having a melting point below the temperature of the molten metal in which the immersion probe is intended for use. A typical temperature range of molten metals is about 2800° F. to about 3100° F., although one skilled in the art will appreciate that the temperature of a given molten metal bath varies with the type of metal or alloy composition. In addition, it may be desirable to have shock absorbing means 16 formed of a material having a melting point below the temperature of the heated gas environment immediately above and around the molten metal bath so that melting or vaporization of the shock absorbing means 16 occurs prior to immersion in the molten metal.

It is preferred that the shock absorbing means 16 comprises a compressible material, such as a natural or synthetic polymer, including rubber, expanded polystyrene, polyurethane and polyethylene, for example. One skilled in the art will recognize that other, similar natural and synthetic polymers may alternatively be used as the shock absorbing material, as well as other compressible materials, such as paper. One skilled in the art will further appreciate that natural or snythetic polymers are relatively inexpensive materials and are easily formed for use as a shock absorbing material in accordance with the present invention.

Preferably, the polymer material is present as an expanded or cellular foam 18, such as foam rubber or polyethylene foam. Preferably also, the polymer foam 18 has a density of about 5 lbs/ft$^3$ to about 12 lbs/ft$^3$. For example, where the material comprising the shock absorbing means 16 comprises polyethylene foam, the shock absorbing means 16 has a density of about 9 lbs/ft$^3$.

The density may be, however, greater than or lesser than the densities described above, depending on the size of the shock absorbing means 16 desired, the compressibility or shock absorbing capacity of the polymer material and the weight of the immersion probe, among other factors. For example, where the immersion probe is relatively heavy, it may be desired to have a polymer foam 18 having a higher density than a polymer foam 18 comprising the shock absorbing means 16 of a relatively light immersion probe. Based on the disclosure herein and the intended use of an immersion probe, one skilled in the art may readily determine the type and density of the polymer foam 18 desired to be used without undue experimentation.

Figure 5:
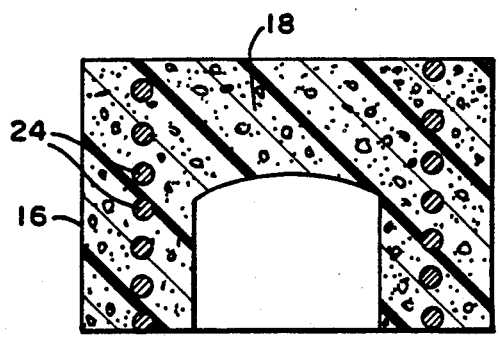
FIG. 5 is an enlarged, inverted cross-sectional view of an alternate embodiment of shock absorbing means in accordance with the present invention.

It will be understood by one skilled in the art that the shock absorbing means 16 may comprise other materials, such as metals and ceramics where, for example, the shock absorbing means 16 comprises a coiled spring 24 or a retractable strut, such as a conventional hydraulic or pneumatic shock absorber, as well as combinations of materials, such as the coiled spring 24, which may comprise a metal or a polymer suitable for coiled springs, and polymer foam 18 shock absorber illustrated in FIG. 5.

Polymer foam is generally available from several manufacturers and may be purchased in block or sheet shapes. Polymer foam pieces may be cut into desired shapes, preferably block shapes, into which an opening or slit may be cut to complementarily receive the protruding first end portion 14 of the probe body 10. Such an opening should be cut to a size large enough to receive the bottom end portion, but small enough to hold the foam block in place by friction when placed on the probe body 10 (see FIG. 2b). The polymer foam 18 may also be held in place by an adhesive that does not substantially interfere with the detecting means in the probe body 10.

Figure 2A:
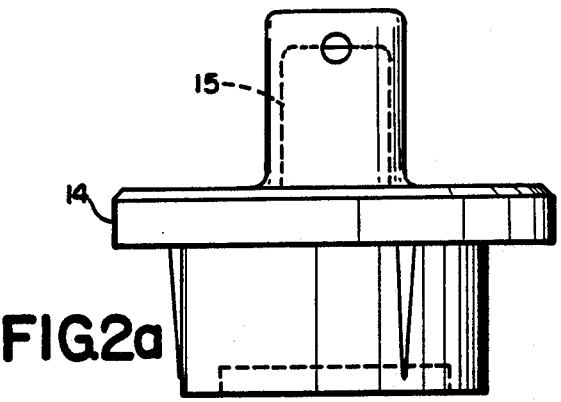
FIG. 2a is an enlarged, inverted side elevational view of a portion of the first end portion of the immersion probe of FIG. 1 with the shock absorbing means removed.
Figure 2B:
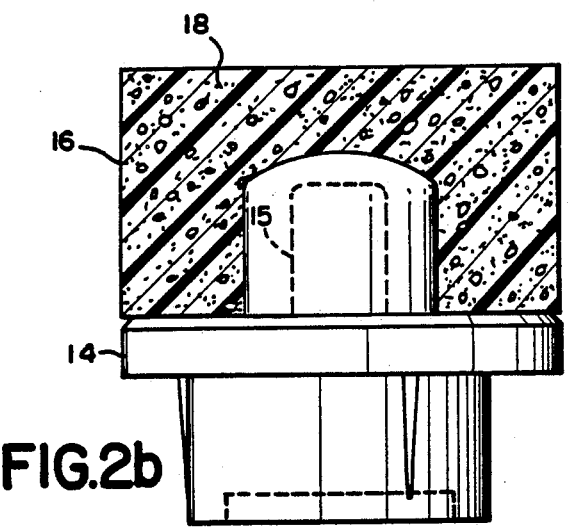
FIG. 2b is an enlarged, inverted side elevational view, partially in section, of the probe portion shown in FIG. 2a showing a cross-sectional view of a first embodiment of shock absorbing means thereon in accordance with the present invention.
Figure 2C:
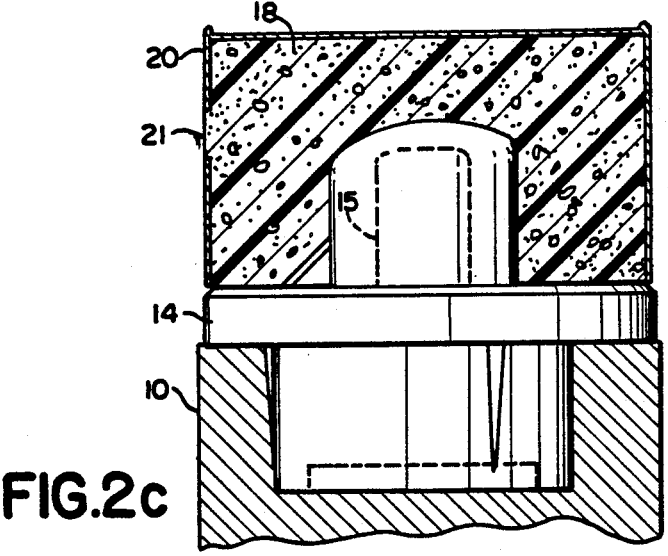
FIG. 2c is an enlarged, inverted partial cross-sectional view showing a slightly different embodiment of the shock absorbing means within a mold proximate the first end portion of an immersion probe.

Alternatively, shock absorbing means 16 comprising a polymer foam 18 may be fitted to an individual immersion probe by molding and curing the polymer foam 18 in place in engagement with and extending from the first end portion 14, as shown in FIG. 2c. Preferably, the polymer foam is molded by placing a mold 20 in engagement with the bottom end portion 14 of the probe body 10. The mold 20 is generally cylindrical with a closed end and with an open end, which is sealed around the periphery of the probe body 10, preferably by applying an adhesive to the mold 20 and the periphery of the first end portion 14. In one embodiment of the present invention, the mold 20 comprises thin walled paper, although other suitable molds, such as molds comprising a rigid polymer or metal, may be used in accordance with the present invention.

Where an adhesive is applied to seal the mold 20 to the bottom end portion 14 of the probe body 10, care should be taken to ensure that the adhesive does not substantially interfere with the detecting means in the immersion probe.

Once the mold 20 is sealed around the periphery of the first end portion 14, the polymer foam 18 may be injected into the mold 20 through insertion means or opening 21 in the mold 20 and allowed to cure. One skilled in the art may readily determine the time and conditions under which the polymer foam should be cured using conventional techniques and apparatus for molding and curing polymer foams.

Figure 3:
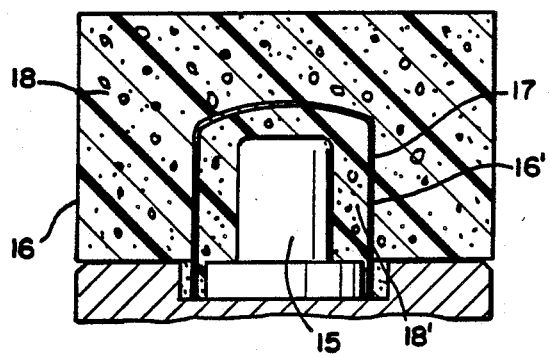
FIG. 3 is an enlarged, inverted side elevational view, partially in section, showing a cross-sectional view of yet another embodiment of the shock absorbing means on the first end portion of an immersion probe and showing shock absorbing means inside the first end portion of the probe in accordance with the present invention.
Figure 4:
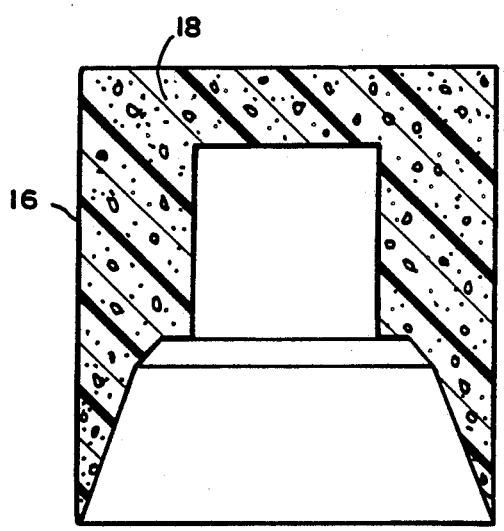
FIG. 4 is an enlarged, inverted cross-sectional view of yet another embodiment of the shock absorbing means according to the present invention.

The particular size and configuration of the shock absorbing means 16 generally may vary, depending on the composition of the shock absorbing means 16, the weight of the immersion probe and the conditions under which the shock absorbing immersion probe is desired to be applied. Generally, where the shock absorbing means 16 comprises a polymer foam 18, the overall configuration of the shock absorbing means 16 may resemble a cover or cap, which is placed over the first end portion 14 of the immersion probe body 10, as illustrated in FIGS. 2b, 4 and 5. In another embodiment of the present invention, shock absorbing means 16 comprises a polymer foam 18, which is positioned within the first end portion 14 of the probe body 10, as illustrated in FIG. 3. Where desired, a second shock absorbing means 16' may also be proximate the first end portion 14 of the within an inner cap 17, such as the polymer foam 18' shock absorbing means 16' illustrated in FIG. 3, to provide additional shock absorption. Other configurations, such as doughnut shapes and closed end shapes may also be used in accordance with the present invention.

It is preferred that the shock absorbing means 16 extend from the probe body 10 in a direction effective to absorb impact loads imposed on the first end portion 14 of the immersion probe and preferably to protect detect means 15 positioned proximate the first end portion 14. For example, where the impact loads imposed upon the first end portion 14 of the probe body 10 come from a direction along the longitudinal axis of the polymer probe body 10, such as when the immersion probe is dropped vertically, it is preferred that the shock absorbing means 16 extend longitudinally from the first end portion 14, as illustrated in FIGS. 1, 2b and 2c. Where the impact loads imposed upon the first end portion 14 of the probe body 10 come from a side direction, it is preferred that the shock absorbing means 16 extend perpendicularly (radially outwardly) from the probe body 10 (not shown). One skilled in the art may readily determine the placement or positioning of the shock absorbing means 16 in relation to the probe body 10 based upon the anticipated impact load forces in accordance with the present invention.

From the foregoing description, it can be seen that the present invention comprises an immersion probe having shock absorbing means proximate the bottom end portion of the probe body. It will be appreciated by one skilled in the art that changes could be made to the embodiments described above without departing from the broad inventive concept thereof. It is understood, therefore, that this invention is not limited to the particular embodiments disclosed but it is intended to cover all modifications that are within the scope and spirit of the invention as defined by the appended claims.

I claim:

1. In an immersion probe for detecting characteristics of a molten metal, including a probe body having a first end portion for immersion into a molten metal bath, and a second end portion coupleable with support means, the probe body having means for detecting characteristics of the molten metal, wherein the improvement comprises shock absorbing means comprised of a compressible material proximate the first end portion of the probe body for absorbing impact loads imposed upon the first end portion of the probe to protect the means for detecting from impact damage when the probe is dropped prior to insertion into the molten metal.

2. The immersion probe according to claim 1, wherein the shock absorbing means melts when exposed to the high temperatures in and around the molten metal bath so as to not substantially interfere with the operation of or the functioning of the detecting means.

3. The immersion probe according to claim 1, wherein the shock absorbing means comprises a material having a melting point below the temperature of the molten metal bath.

4. The immersion probe according to claim 1, wherein the shock absorbing material comprises a polymer.

5. The immersion probe according to claim 4, wherein the polymer comprises rubber.

6. The immersion probe according to claim 4, wherein the polymer comprises expanded polystyrene.

7. The immersion probe according to claim 4, wherein the polymer comprises polyurethane.

8. The immersion probe according to claim 6, wherein the polymer comprises polyethylene.

9. The immersion probe according to claim 8, wherein the polyethylene has a density of about 5 lbs/ft$^3$ to about 12 lbs/ft$^3$.

10. The immersion probe according to claim 4, wherein the polymer has a density sufficient to protect the first end portion of the probe from impact damage.

11. The immersion probe according to claim 1, wherein the shock absorbing means comprises a spring member.

12. The immersion probe according to claim 11, wherein the spring member is made of a polymer.

13. The immersion probe according to claim 11, wherein the spring member is made of metal.

* * * * *